United States Patent
Steiger et al.

(10) Patent No.: US 11,342,056 B2
(45) Date of Patent: May 24, 2022

(54) METHOD AND APPARATUS FOR CHARACTERISTIC MONITORING IN CONJUNCTION WITH A MODE OF CONTINUOUSLY MEASURED BLOOD GLUCOSE VALUES AND COMPUTER PROGRAM PRODUCT

(71) Applicant: Roche Diabetes Care Inc., Indianapolis, IN (US)

(72) Inventors: Bernd Steiger, Roemerberg (DE); Juergen Rasch-Menges, Schwetzingen (DE)

(73) Assignee: Roche Diabetes Care Inc., Indianapolis, IN (US)

( * ) Notice: Subject to any disclaimer, the term of this patent is extended or adjusted under 35 U.S.C. 154(b) by 496 days.

(21) Appl. No.: 14/967,155

(22) Filed: Dec. 11, 2015

(65) Prior Publication Data
US 2016/0097760 A1     Apr. 7, 2016

Related U.S. Application Data

(63) Continuation of application No. PCT/EP2014/062467, filed on Jun. 13, 2014.

(30) Foreign Application Priority Data

Jun. 13, 2013    (EP) .................................. 13171897

(51) Int. Cl.
*G16H 20/10*      (2018.01)
*A61B 5/00*       (2006.01)
(Continued)

(52) U.S. Cl.
CPC ......... *G16H 20/10* (2018.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| | | | |
|---|---|---|---|
| 4,647,918 A * | 3/1987 | Goforth | ............... A43B 3/0005 340/573.1 |
| 2003/0208113 A1* | 11/2003 | Mault | .................... A61B 5/415 600/316 |

(Continued)

FOREIGN PATENT DOCUMENTS

| | | |
|---|---|---|
| CN | 103003819 A | 3/2013 |
| DE | 102004057503 A1 | 6/2006 |

(Continued)

OTHER PUBLICATIONS

Albisser, A. M. A graphical user interface for diabetes management that integrates glucose prediction and decision support. Diabetes Technology and Therapeutics 7, 264-273 (2005).*

(Continued)

*Primary Examiner* — Soren Harward
(74) *Attorney, Agent, or Firm* — Bose McKinney & Evans LLP

(57) ABSTRACT

A method for characteristic monitoring in conjunction with a mode of continuously measured blood glucose values, in a monitor apparatus provided with a processor, a memory, a data interface, an input device, and a signaling device, the method comprising: providing a first set of event specific characteristics assigned to a first event, the first set of event specific characteristics being different from a second set of event specific characteristics assigned to a second event which is different from the first event, receiving blood glucose value data performing a safety check by comparing the first set of event specific characteristics to present characteristics derived from the blood glucose value data and/or the characteristic values, generating a warning signal (Continued)

or generating a safety signal, and outputting an output signal. A monitor apparatus is also disclosed.

27 Claims, 5 Drawing Sheets

(51) Int. Cl.
*A61B 5/145* (2006.01)
*G01N 33/487* (2006.01)
*G01N 33/49* (2006.01)
*G08B 21/18* (2006.01)

(52) U.S. Cl.
CPC ....... *G01N 33/48792* (2013.01); *G01N 33/49* (2013.01); *G08B 21/182* (2013.01)

(56) References Cited

U.S. PATENT DOCUMENTS

| | | | | |
|---|---|---|---|---|
| 2006/0264895 A1* | 11/2006 | Flanders | ............... | A61B 5/4839 604/504 |
| 2008/0021436 A1* | 1/2008 | Wolpert | ............ | H01L 23/49548 600/365 |
| 2008/0228055 A1* | 9/2008 | Sher | ................... | A61B 5/14532 600/365 |
| 2008/0234992 A1* | 9/2008 | Ray | ......................... | G06F 17/18 703/2 |
| 2009/0192751 A1* | 7/2009 | Kamath | ............. | A61B 5/14532 702/104 |
| 2010/0145262 A1* | 6/2010 | Bengtsson | ......... | A61B 5/14532 604/66 |
| 2011/0011399 A1* | 1/2011 | Wolpert | ............. | A61B 5/14532 128/203.14 |
| 2011/0124996 A1* | 5/2011 | Reinke | ............... | A61M 5/14248 600/365 |
| 2011/0193704 A1* | 8/2011 | Harper | ................. | A61B 5/7275 340/573.1 |
| 2012/0078067 A1* | 3/2012 | Kovatchev | ............. | G16H 50/50 600/301 |
| 2013/0078601 A1 | 3/2013 | Angelides | | |
| 2013/0130215 A1 | 5/2013 | Bock et al. | | |
| 2013/0187780 A1* | 7/2013 | Angelides | ............ | A61B 5/0002 340/573.1 |
| 2013/0274183 A1* | 10/2013 | Kim | .................... | A61M 5/1723 514/5.9 |

FOREIGN PATENT DOCUMENTS

| | | | |
|---|---|---|---|
| EP | 2256495 A2 | 12/2010 | |
| WO | WO 2010/091129 A1 | 8/2010 | |
| WO | WO 2012/010298 A1 | 1/2012 | |
| WO | WO-2012010298 A1 * | 1/2012 | ........... A61B 5/1118 |
| WO | WO-2012019746 A1 * | 2/2012 | ........... A61B 5/0002 |

OTHER PUBLICATIONS

First Office Action in Chinese Patent Application 201480033524.9 dated May 2, 2017.
International Search Report; PCT/EP2014/062467; dated Sep. 23, 2014; 3 pages.
Gross et al., "Performance Evaluation of the MiniMed Continuous Glucose Monitoring System During Patient Home Use", Diabetes Technology & Therapeutics, vol. 2 No. 1, p. 49-56, 2000.
Office Action in Canadian Patent Appiication 2,912,162 dated Sep. 17, 2018 (4 pages).
Office Action in EP Patent Application 14 739 696.4 dated Feb. 21, 2018 (10 pages).
Response in EP Patent Application 14 739 696.4 dated Jul. 22, 2016 (11 pages).
Gross et al., "Performance Evaluation of the MiniMed Continuous Glucose Monitoring System During Patient Home Use", Diabetes Technology & Therapeutics, vol. 2 No. 1, p. 49-56, 2000 and Appendix of citations.

* cited by examiner

METHOD AND APPARATUS FOR CHARACTERISTIC MONITORING IN CONJUNCTION WITH A MODE OF CONTINUOUSLY MEASURED BLOOD GLUCOSE VALUES AND COMPUTER PROGRAM PRODUCT

CROSS REFERENCE TO RELATED APPLICATIONS

This is a continuation of application serial no. PCT/EP2014/062467 filed Jun. 13, 2014 and which claims priority from application serial no. EP 13 171 897.5 filed Jun. 13, 2013, the disclosures of which are both hereby incorporated herein by reference.

BACKGROUND

The invention relates to a method and apparatus for characteristic monitoring in conjunction with a mode of continuously measured blood glucose values and computer program product.

Such methods and systems are used in order to monitor characteristics of patients' measured blood glucose values in the context of events. The objective is to give the patient information which enable the patient to deal with his blood glucose values in an improved and appropriate manner.

For people suffering from diabetes, in particular diabetes mellitus, it is especially important for them to keep their blood glucose values constantly at a particular level. A precondition for this is knowledge of their blood glucose value which is therefore measured using a blood glucose measuring device set up for this purpose. Blood glucose measuring devices are known in various embodiments.

If it is determined, on the basis of the measured values, that the blood glucose value has exceeded the recommended level, medicine is administered, for example by means of insulin injection or the oral administration of Metformin, an oral antidiabeticum. If the blood glucose values fall below the ideal or recommended level, sugar must be orally ingested, for example through food or drink. If the ideal level is exceeded for an extended period of time, there is the danger of serious health complications such as blindness, kidney damage, limbs having to be amputated or neuropathy. If the exceeding of the prescribed blood glucose level is for a short time only but considerable, this can lead to nausea, dizziness, sweating or even conditions of confusion. Thus, it is particularly important for a diabetic to know his blood glucose values at all times so that he is able to implement the appropriate measures to avoid the blood sugar values deviating from the ideal levels.

A blood glucose measuring device with which the blood glucose values of diabetics can be measured is known, for example from the document DE 10 2004 057 503 A1 and is sold by the applicant under the registered trade mark, Accu-Chek.

Blood glucose measurements may be made according to a continuous measurement regime. Such measurements are also known as CGM measurements (CGM—Continuous Glucose Monitoring). In this process, the blood glucose values are measured continuously in a continuous time period such that, for example, the progress of the blood glucose value can be collected over an entire day or week. The analysis of the measured blood glucose values can provide for the determination of several day trends. In this way it is possible to determine blood glucose fluctuations dependent on the time of day. A disadvantage of the continuous blood glucose measurements is firstly, due to the continuous measurements, it can lead to high costs and secondly that it leads to discomfort for the diabetic whereby the latter is caused by the permanent wearing of a subcutaneous sensor. This can lead to infections at the point of entry, intolerance of the plaster or skin irritation which prevents the device being worn permanently or for a long period of time, for example several months. A continuous measurement of the blood glucose values is described, for example, in the document, Gross et al., "*Performance Evaluation of the MiniMed Continuous Glucose Monitoring System During Patient Home Use*", Diabetes Technology & Therapeutics, 2 (2000)49.

On the basis of the quantity of available data on the current metabolic status of the user, CGM systems may provide assessment of the present situation and forecasts for the further course of the blood glucose level. In the analysis of the CGM data, after filtering and smoothing, the momentary situation and the momentary rate of change may be checked for adherence to predetermined limit values. The predetermined limit values are only incompletely adapted to the individual framework conditions. CGM used in this way can ensure dense monitoring in terms of time, but there is no further support for the user regarding planned, currently started or still running events or activities.

Document US 2013/0130215 A1 discloses a system and a method for considering the effects of aerobic exercise on blood glucose levels for individuals. The system comprises a computing device for generating a prediction of future blood glucose levels for the individual at least partly based on an exercise model, wherein the exercise model is based on parameters that are independent of intensity of the aerobic exercise, and a means for taking an action, namely controlling of an insulin pump, at least based on the prediction from the exercise model.

SUMMARY

The disclosed methods and apparatus provide improved technologies for characteristic monitoring in conjunction with a mode of continuously measured blood glucose values.

One embodiment comprises a method for characteristic monitoring in conjunction with a mode of continuously measured blood glucose values, in a monitor apparatus provided with a processor, a memory, a data interface, an input device, and a signaling device, includes providing a first set of event specific characteristics of a continuous blood glucose monitoring assigned to a first event in the processor, the first set of event specific characteristics being different from a second set of event specific characteristics of the continuous blood glucose monitoring assigned to a second event which is different from the first event; receiving blood glucose value data comprising continuously measured blood glucose values by the processor; providing the blood glucose value data and/or characteristic values derived from the blood glucose value data to the processor; performing a safety check by comparing the first set of event specific characteristics to present characteristics of the continuous blood glucose monitoring derived from the blood glucose value data and/or the characteristic values by the processor; generating by the processor a warning signal indicating one of an event activity related to the first event shall not be started and an event activity related to the first event and started before shall not be continued, if one or more of the present characteristics do not match the assigned characteristic from the first set of event specific characteristics, otherwise generating a safety signal; and outputting an output signal according to the warning signal or the safety signal by the signaling device, the output signal comprising at least one of a visual signal and an acoustic signal.

Another embodiment comprises a monitor apparatus for safety characteristic monitoring in conjunction with a mode of continuously measured blood glucose values, the apparatus comprising a processor, a memory, a data interface, an input device, and a signaling device, and the processor being configured to perform the following steps: providing a first set of event specific characteristics of a continuous blood glucose monitoring assigned to a first event, the first set of event specific characteristics being different from a second set of event specific characteristics of the continuous blood glucose monitoring assigned to a second event which is different from the first event; receiving blood glucose value data comprising continuously measured blood glucose values; receiving the blood glucose value data and/or characteristic values derived from the blood glucose value data; performing a safety check by comparing the first set of event specific characteristics to present characteristics of the continuous blood glucose monitoring derived from the blood glucose value data and/or the characteristic values; generating a warning signal indicating one of an event activity related to the first event shall not be started and an event activity related to the first event and started before shall not be continued, if one or more of the present characteristics do not match the assigned characteristic from the first set of event specific characteristics, otherwise generating a safety signal; and providing the warning signal or the safety signal to the signaling device for outputting an output signal according to the warning signal or the safety signal by the signaling device, the output signal comprising at least one of a visual signal and an acoustic signal.

Yet another embodiment comprises a computer program product, stored on a storage medium and configured to perform one or more of the methods disclosed herein during operation on a data processing device.

Still further variations of these embodiments are disclosed herein.

A method for characteristic monitoring in conjunction with a mode of continuously measured blood glucose values in a monitor apparatus is provided. The monitor apparatus comprises a processor, a memory, a data interface, an input device, and a signaling device. In the method a first set of event specific characteristics of a continuous blood glucose monitoring assigned to a first event is provided in the processor. With respect to one or more characteristics, the first set of event specific characteristics is different from a second set of event specific characteristics of the continuous blood glucose value monitoring assigned to a second event which is different from the first event. The event specific characteristics may also be referred to as event conditioned characteristics. Examples for such events are car driving and physical exercise. At least one of the first and second events may comprise a plurality of sub-events.

The first and second event specific characteristics, for example, may be different with respect the value, a range of value, a value variation and/or a trend of value. The set of event specific characteristics may comprise a plurality of defined conditions, values, value trend and/or value variation, e.g. range, required to be met by a user before starting, at start and/or during some event related activity, for example physical activity (sport).

Blood glucose value data comprising continuously measured blood glucose values are received by the processor. The data may be received via the data interface from an external device, for example, a blood glucose measuring device. Also, the continuously measured blood glucose values may be received from some other data storage device, or may be received from the memory of the monitor apparatus.

The processor is performing a safety check by comparing the first set of event specific characteristics to present characteristics of the continuous blood glucose monitoring. The present characteristics are derived, by the processor, from the blood glucose value data and/or from the characteristic values which in turn are derived from the blood glucose value data. For determining of the characteristic values the blood glucose value data provide a raw data set analyzed for deriving the characteristic values. The present characteristics may refer to one or more discrete values and/or one or more sets of continuous values representing a continuous course (curve). Both the discrete values and the set of values may comprise future values representing a prediction or prognosis for some future time or future time period after the present determination of the present characteristics.

In the course of the safety check it is checked whether the present characteristics of the continuous blood glucose monitoring meet the criteria assigned to the first event. The safety check may comprise comparing electronic data representing graphical curves. As an alternative or in addition, characteristic parameters of curves, e.g. trend or slope and/or local maximum or minimum, may be compared.

By the processor a warning signal is generated if one or more of the present characteristics do not match the assigned characteristic(s) from the first set of event specific characteristics, otherwise generating a safety signal which is indicating a "being safe situation" to the user. The warning signal is indicating that one of an event activity related to the first event shall not be started and an event activity related to the first event and started before shall not be continued. The safety signal shows that all present characteristics match the assigned characteristic of the set of characteristics of the event or set of events under consideration, or for a required selection of characteristics the present characteristics match the assigned characteristic of the set of characteristics. The electronic warning/safety signal may be configured to control output of an output signal. By the apparatus the output signal according to the warning signal or the safety signal is outputted via the signaling device. The output signal comprises at least one of a visual signal, haptic signal and an acoustic signal. For example, one of "STOP", "DO NOT START", and "DO NOT CONTINUE" may be outputted as the warning signal. "START" or "CONTINUE" provide for examples of a safety signal. Thereby the user may be informed whether the event for which the specific set of characteristics was checked against the present characteristics is allowed or not. Also, the user may be informed whether he is allowed to continue or not with an event activity started before.

By the proposed technologies, prior to starting an event, for the user a situation may be avoided in which the event is started despite specific characteristics of the continuous blood glucose value monitoring indicate that the event shall not be started.

Events for which the one or more sets of characteristics are provided may be, for example, a physical training or a (long distance) car drive. Other events may refer to travelling in general (not only car journeys), sporting activities such a hiking, bicycle tours, fitness training etc., episodes of illness, menstrual periods, stress, emotional strain, time zone displacement, shift work, and/or even food intake resp. insulin administration or other medication etc.

The characteristic monitoring apparatus may be a mobile or handheld device such as a mobile personal computer, a glucose meter or a mobile smart phone. Also, the characteristic monitoring apparatus may be a desktop device, e.g. a desktop computer that may be used together with a stationary training bike.

The first set of event specific characteristics is provided to the processor in response to receiving user input data via the input device. The user input data may be received in the monitor apparatus by means of an input device, for example a key pad, touch pad or by speech recognition. The input data may request a set of event specific characteristics of a continuous blood glucose monitoring assigned to an event or a set of sub-events to be provided. As an alternative or in addition, the user input data may provide for setting and/or adjustment of the set of event specific characteristics.

The user input data may comprise event selection data selecting an event for which a starting first set of event specific characteristics is provided in the memory. Information about the starting first set of events specific characteristics may be stored in different configurations in the memory.

A menu may be provided to the user on the signaling device which may comprise a display. From the menu the user may select one or more events for which the starting set of events specific characteristics is stored in the memory. In an embodiment, in response to a user input the user may be requested to input value data for the event specific characteristics. Thereby, the user may configure the event specific set of characteristics.

With respect to at least one of the first set of event specific characteristics and the second set of event specific characteristics, the user input data may comprise event definition data defining or redefining one or more characteristics from the first set of event specific characteristics. The user may define whether a specific characteristic is part of the set of event specific characteristics or not. And event specific characteristic may be added or deleted from the proposed set of event specific characteristics by the user. In addition or as an alternative, the user may define the value and/or the value range for one or more event specific characteristics.

With respect to at least the first set of event specific characteristics, the processor may be implementing a self-learning procedure by analyzing former events and/or current events and adjusting one or more characteristics from the first set of event specific characteristics. In this self-learning process the monitor apparatus may analyze the course of events in the past and adjust one or more event specific characteristics. For example, if the conclusion is made that some event specific characteristic defined for the former event has not provided the expected trend or course of the continuously monitored blood glucose level, such event specific characteristic may be increased or decreased in the present set of event specific characteristics. In another example, an average value or any other statistical evaluation of the values of an event specific characteristic may be determined for adjusting the event specific characteristic in the present set of event specific characteristics.

At least one of the first set of event specific characteristics and the second set of event specific characteristics may be provided with a set of weighted event specific characteristics. It may be provided that one or more characteristics have to be matched by the present characteristics more exactly than others. Also, a subset off the event specific characteristics may be required to be matched in any case for providing this safety signal, while other event specific characteristics do not. In another case, one or more event specific characteristics may be required to be matched exactly, while others only have to be with in the variation limit of the event specific characteristics of the set of characteristics.

The steps of performing the safety check, generating the warning/safety signal and providing the output signal may be repeated by the processor after receiving a user input indicating that the event activity related to the first event was started. One or more of the steps may be repeated after certain time periods. The user may set such time periods for repeating one or more steps by input data. In addition or as an alternative, the safety check may be an on-going procedure of the apparatus or such repeating time periods may automatically be provided by the apparatus. In the memory of the monitor apparatus there may be information stored about such event specific repeating time periods.

In case of generating the warning signal, a help signal may generated by the processor and outputted by the signaling device, the help signal providing information about proposed user action aiming at matching of the present characteristics with the assigned characteristic from the first set of event specific characteristics. The help signal may comprise a text message outputted via a display. For example, it may be proposed to the user to take some food/drink and/or have a rest. Prior to an event, by the help information guidance may be provided to the user for finally matching the event specific characteristics which are currently not fulfilled (pre-event phase). As an alternative or in addition, the help signal may be provided by the processor in the course of an ongoing event. Again, the user may be asked to take some food or get insulin medication, for example during a long car driving period.

If at a point in time t1 prior to an event starting in the future it is found that one or more of the present characteristics do not match the assigned characteristic(s) from the first set of event specific characteristics the processor may initiate at least one other safety check prior to the proposed event at a point in time t2 which is closer to the proposed event starting point. Such safety check may also be referred to follow-up safety check prior to the proposed event starting. For example, the user taking action proposed by the helping signal may now be eligible (ready) for the event. The present characteristics at the point in time t2 may fit the required characteristics.

At least one of first set of event specific characteristics and the second set of event specific characteristics may comprise one or more characteristics selected from the following group: blood glucose value from a continuous measurement, trend or slope of a continuous blood glucose monitoring curve, time of insulin medication, insulin medication information, meal time, and meal information. Meal information may indicate an amount of carbohydrate. Other characteristics may be at least one of: start of an event, time to an event, intensity of an event, e.g. exercise, planned duration of an event, and end of an event. Furthermore, other influencing factors like medication, stress and/or menstruation, may apply.

BRIEF DESCRIPTION OF THE DRAWINGS

In the following, the invention will be described in further detail, by way of example, with reference to different embodiments. The figures show.

Figure 1:
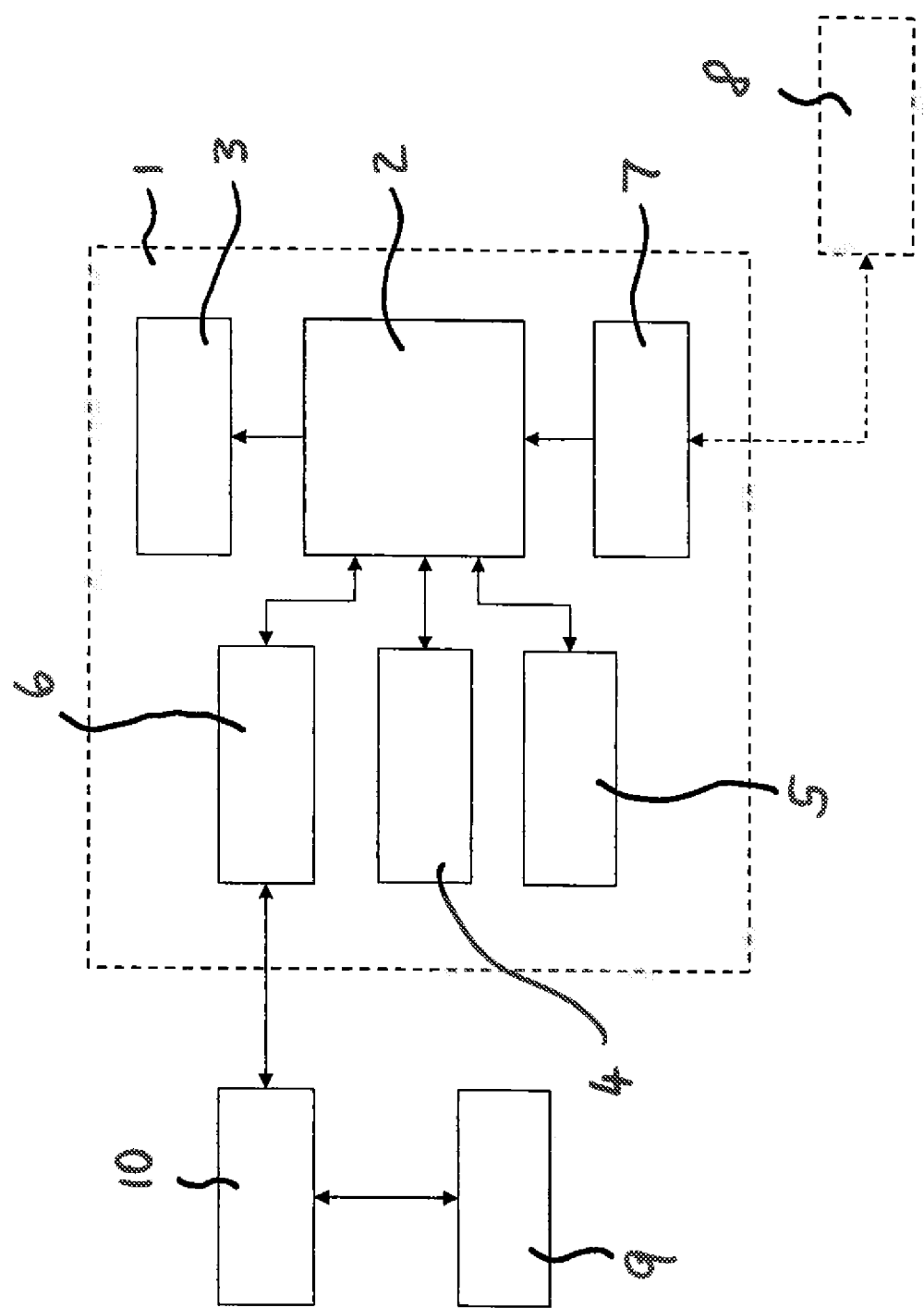
FIG. 1 a schematic representation of an apparatus for characteristic monitoring in conjunction with a mode of continuously measured blood glucose values, FIG. 2 a schematic presentation of a display presenting an event menu, FIG. 3 a schematic presentation of a display presenting an a characteristic menu presenting event specific characteristics, FIG. 4 a continues blood glucose value curve in dependence on time for a specific situation, FIG. 5 a continues blood glucose value curve in dependence on time for a specific situation, FIG. 6 a continues blood glucose value curve in dependence on time for another specific situation, FIG. 7 a continues blood glucose value curve in dependence on time for some other specific situation, and FIG. 8 a continues blood glucose value curve in dependence on time for still another specific situation.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

FIG. 1 is a block diagram of an apparatus for characteristic monitoring 1 in conjunction with a mode of continuously measured blood glucose values in accordance with an embodiment of the present invention. The characteristic monitoring apparatus 1 may be a mobile or handheld device such as a mobile personal computer, a glucose meter or a mobile smart phone. Also, the characteristic monitoring apparatus 1 may be a desktop device, e.g. a desktop computer. The characteristic monitoring apparatus 1 is provided with a processor 2 which is connected for data exchange with a display device 3, an input device 4 such as a keypad, a memory 5, and a data interface 6.

In the embodiment shown in FIG. 1, the characteristic monitoring apparatus 1 comprises a sensor input 7 connectable to a glucose sensor device 8. The sensor input 7 and the glucose sensor device 8 are provided optionally, e.g. in the case that the characteristic monitoring apparatus 1 is implemented by a continuous glucose meter. The glucose sensor device 8 employs a sensor that produces a measured glucose level of the user or produces a signal that corresponds to a measured glucose level of the user. The glucose sensor device 8 communicates these signals to the characteristic monitoring apparatus 1 that may be designed to interpret these signals to produce a characteristic reading or value for the user, i.e. a measurement of the characteristic. The sensor signals enter the characteristic monitoring apparatus 1 through the sensor input 7 and through the sensor input 7 the signals are conveyed to the processor 2. If such embodiment is provided, the processor 2 may determine and manipulate the sensor readings.

In addition, the characteristic monitoring apparatus 1 may provide additional functions that will aid in the treatment regime to which the characteristic reading applies. For example, but not limited to, the characteristic monitoring apparatus 1 may track meals, exercise and other activities which affect the treatment of diabetes.

The other components of the characteristic monitoring apparatus 1 support the processor 2 in performing functions. The memory 5 is used to store data and instructions used by the processor 2. The input device 4 which may comprise a keypad is used to receive direct input from the user and the display device 3 such as a liquid crystal display (LCD), or the like, is used to relate information to the user. The data interface 6 may be provided with a digital input/output (I/O) port.

The data interface 6 can be used for the characteristic monitoring apparatus 1 to communicate with an external device 9 such as a computer. To facilitate communication, the characteristic monitoring apparatus 1 may interface with the external device 9 through a communication station 10 that can serve a docking station for the characteristic monitoring apparatus 1, for example. In some embodiments, the data interface 6 within the characteristic monitoring apparatus 1 may be directly connected to the external device 9. Through the communication link, data may be downloaded from the characteristic monitoring apparatus 1. Thus, advanced analysis can be performed on a computer freeing the memory 5 within the characteristic monitoring apparatus 1. Data such a characteristic settings and programs can also be downloaded to the characteristic monitoring apparatus 1. In this way, the characteristic monitoring apparatus 1 can be conveniently reprogrammed without requiring manual entry by the user. Especially, continuously measured blood glucose values may be received by the characteristic monitoring apparatus 1.

Following, further aspects of a method for characteristic monitoring in conjunction with a mode of continuously measured blood glucose (CGM) values are described.

CGM value data are received in the characteristic monitoring apparatus 1, e.g. through the data interface 6. The CGM data may be "contextualised" with further background information. The CGM data are to be used for the event specific support of the user in everyday decisions. This support may include the automatic generation of information for the user relating to current actions and evaluations of the current metabolic situation ("advice"), as well as information about future situations ("forecast") and their evaluation, and also information about how a negative development can be prevented through taking early action. The user may be kept up to date by way of alarms and/or reminders. The relevant metabolic situations may be shown in a suitable graphic form through highlighting etc. and/or also through other suitable response mechanisms such as visual and/or acoustic signals.

Figure 2:
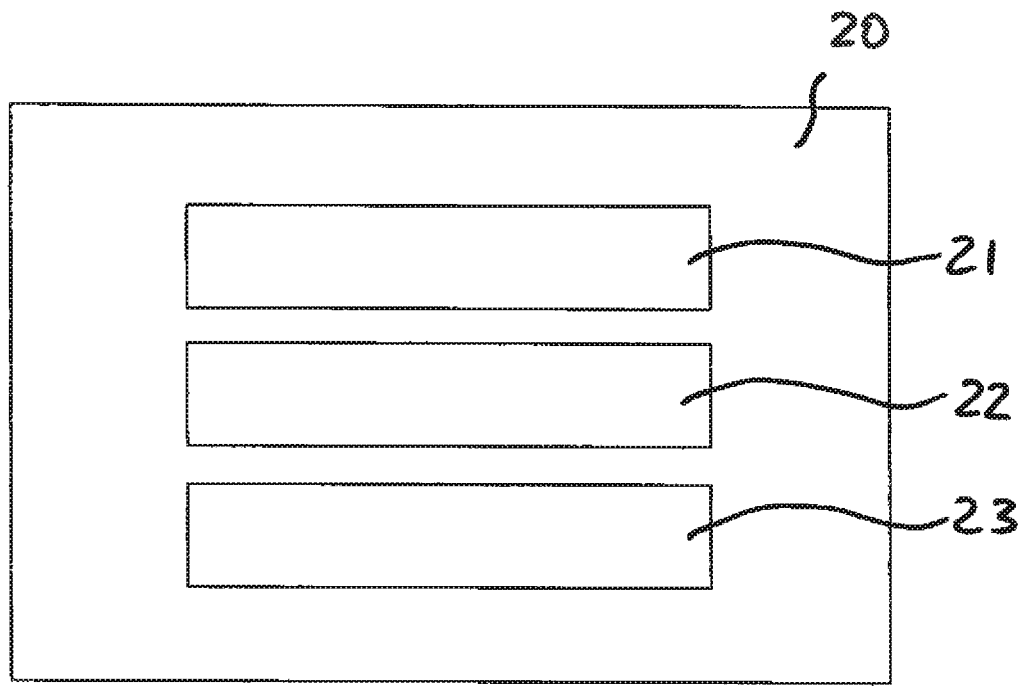

Therefore, an event related safety check for selected events is provided by the characteristic monitoring apparatus 1. Referring to FIG. 2, in response to receiving a user request, on the display device 3 an event menu 20 is shown. The event menu 20 comprises different events 21, . . . , 23 for user election. The different events 21, . . . , 23 may refer to a physical training or a long distance car drive. Other events may refer to travelling in general (not only car journeys), sporting activities such a hiking, bicycle tours etc., meals, episodes of illness, menstrual periods, stress, emotional strain, time zone displacement, and/or shift work.

The user of the characteristic monitoring apparatus 1 may be allowed to amend the menu 20, e.g. for generating or including a new event in the list, for revising the different events 21, . . . , 23 that are already present and/or for removing those events no longer required from the menu 20.

Figure 3:
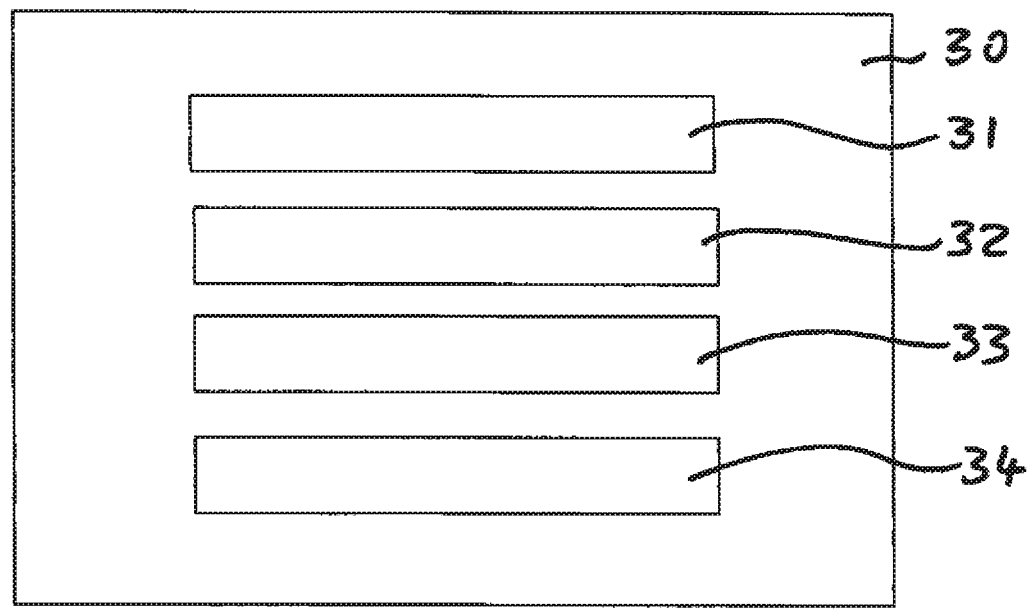

The selection of one of the different events 21, . . . , 23 can take place in that this event has already started at the given point in time, i.e. this safety check should immediately take place, or in that for a future event the necessary preconditions for smooth implementation through still to be determined measures are created, or the presence of these preconditions is checked for. In each case, for the selected event it is checked in detail whether event specific characteristics such as the CGM value as such, the CGM curve shape, pattern, i.e. the typical time sequences of high/low CGM values and/or their changes, environment data satisfy certain requirements so that the planned activity can be securely started and implemented. FIG. 3 shows a schematic representation of a characteristic menu 30 listing event-specific characteristics 31, . . . , 34. Again, the user may be allowed editing the event specific characteristics 31, . . . , 34 by inputting user inputs through the input device 4.

To support pending requirements such as travel, sport, change of medication; longer car journey, walk, or woman's menstrual cycle, characteristics are defined which allow the patient to securely carry out the event over a planned period. The characteristic monitoring apparatus 1 allows the event-specific characteristics to be adjusted. In this way the user can define characteristics for repeatedly occurring events which are automatically checked by the characteristic monitoring apparatus 1 when the event becomes due.

The characteristic monitoring apparatus 1 automatically and event-specifically suggests, usually in response to a request received by the characteristic monitoring apparatus 1, a recommended characteristic setting such as the characteristic menu 30 to the user and/or allow the user to select from a list of characteristic suggestions. More particularly the prevent-specific proposed characteristic setting has already been optimised with regard to the selected event. For example, event-related settings for a characteristic setting are stored in the memory 5 of the characteristic monitoring apparatus 1, which are optimised for events. Further differentiations with regard to the duration and/or nature of events can also be predefined and stored in the characteristic monitoring apparatus 1.

Furthermore, for predefined events a different characteristic weighting and/or different values ranges to be observed can be set for the parameters. If the characteristics for an event are set the characteristic monitoring apparatus 1 checks whether the user fulfils the predetermined parameters for the planned activity. Such pre-event characteristic setting may also be referred to as entry criterion. The safety check is automatically done by the characteristic monitoring apparatus 1 in response to receiving present data which may comprise current blood glucose values, time information and/or event related information such as current intensity of a physical exercise. Based on such current information the characteristic monitoring apparatus 1 compares present characteristic values to the characteristic monitoring apparatus 1 selected before by processing the current information data and the characteristic monitoring apparatus 1 by the processor 2. If the patient does not satisfy the entry conditions the characteristic monitoring apparatus 1 can inform the patient thereof and/or suggest action options.

The characteristic monitoring apparatus 1 may allow automatic optimisation of the characters which can thus be adapted to the relevant event. For this the apparatus 1 can perform an analysis of the same or similar events and its event-related characteristics in the past. If the patient has implemented an event in which all entry criteria were fulfilled in a past event but the patient does not exhibited a desired CGM value/course for a present event, the apparatus 1 can re-optimise the character setting or suggest changing the character settings to the user.

It may also be provided for the characteristic monitoring apparatus 1 to warn the user if in the case of an event the entry parameters were not fulfilled in the past or there were no adherence conditions, also resulting in an undesirable CGM value/course. The direct consequence of incorrect behaviour can thus be pointed out to the user by signalling the user through the display device 3.

In addition or as an alternative, the characteristic monitoring apparatus 1 recognise the action patterns of a user and thereby automatically remind the user of pending events. For example if the patient regularly engages in a sport in the morning, the system can remind the user of the pending event in good time. If the user confirms the event the entry criteria are then checked.

Furthermore the user can select an event containing predetermined entry and adherence criteria that are event-specific. For example the slope and value of the CGM curve must lie within predefined limits if a certain sporting activity is planned. In addition these criteria can, as described, be adapted and optimised through an analysis of the same events in the past. If, for example, the blood glucose level falls too sharply during an event, e.g. morning jogging, even though the patient has fulfilled all the event-specific characteristics, the apparatus 1 can automatically carry out a correction of the parameter settings. For example, the limit value for the absolutely measured glucose value and/or the range of parameters describing a glucose progression such as slope can be adapted or suggested for adaptation by a user information on the display device 3.

For example, the user can enter the event "long car journey" to check whether the current metabolic situation of the user allows safe driving. Via the input device 4, the data interface and/or the sensor input 7 and/or from the memory 5, the processor 2 receives data related to the user's current situation. The processor 2 will process such current data and check it against the event-specific characteristics related to the event which shall be started by the user (entry criterion). In another scenario, the user may request characteristic monitoring apparatus 1 to set safe limit values for the metabolic characteristics for the duration (course) of the journey and to continuously monitor that they are being adhered to (adherence criterion).

The result of the safety check can be given to the user as a "starting signal" that it is now safe to start the selected activity. Alternatively the proposed system can acknowledge to the user that his/her metabolic situation is currently in a "safe range". If the user combines several overlapping events the system can follow these but only if there have been suitable measurements in the past.

Further measures signalled to the user, e.g. through the display device 3, can include: indication to have suitable snacks available for the journey, automatic alarms to take breaks with meals, information on how insulin doses should be adjusted, warning that the quality of the current CGM value does now allow further evaluation and a CGM measurement with SMBG (SelfMonitoring Blood Glucose) for new calibration is urgently required, warning information about how the current metabolic situation must be corrected before starting on the car journey etc. The SMBG measurement is done for calibration. Following, the CGM measurement may be continued. In the course of CGM at least about every five minutes a measured blood glucose value may be provided.

In addition to the above request as to whether a car journey can now be started, the characteristic monitoring apparatus 1 may be configured to provide automated support in a pre-event time period. For example, if the user enters into the apparatus 1 in the morning that a longer car journey is planned in the afternoon, the characteristic monitoring apparatus 1 provides information about sensible preparatory measures and can adjust limit values so that at the start of the event "car journey" the metabolic situation can be set to the optimum situation for continuous monitoring for this use, e.g. by recommending meals, more frequent administration of smaller quantities of insulin, and/or calibration of the CGM system if the current quality is not sufficient.

In another embodiment, a mode of retrospective analysis of events is implemented by the characteristic monitoring apparatus 1. In the mode, a stored CGM sequence may be analysed. Here, the set of characteristics used at that time, for example, entry criterion and/or adherence criterion can be checked and any adaptions for the individual framework conditions of the user carried out and general optimisation of the typical setting values for future similarly stored applications can take place. The retrospective evaluation thus also provides correlation between used entry and adherence criteria and the percentage of successfully completed events used as the forecast basis for planning future events. For example, in case of periodically recurring events such as a morning exercise the apparatus 1 may automatically recognises and set optimum marginal conditions based on the assumption "as always the user carries out his sporting activity at 07:30 in the morning". In cases of doubt this is automatically queried with the user.

Referring to FIGS. 4 to 8, continues blood glucose curves are shown in dependence on time for different situations. In addition, insulin medication (IU) and carbohydrate intake (g) are indicated referring to labels on the upper right hand side and the lower right hand side, respectively.

In the FIGS. 4 to 8, curve A represents the continues blood glucose curve progression until "present", curve A* represents an expected curve progression or trend of the continues blood glucose for a future time period, e.g. the next hour, curves C1, C2 represent an upper and an lower limit for the continues blood glucose in case of the event "exercise", and curves D1, D2 represent an upper and an lower limit for the continues blood glucose in case of the event "car driving". For the embodiments shown, curve A* was determined by a linear extrapolation. Other methods known as such may be applied for determining an expected or predicted curve progression/trend.

Figure 4:
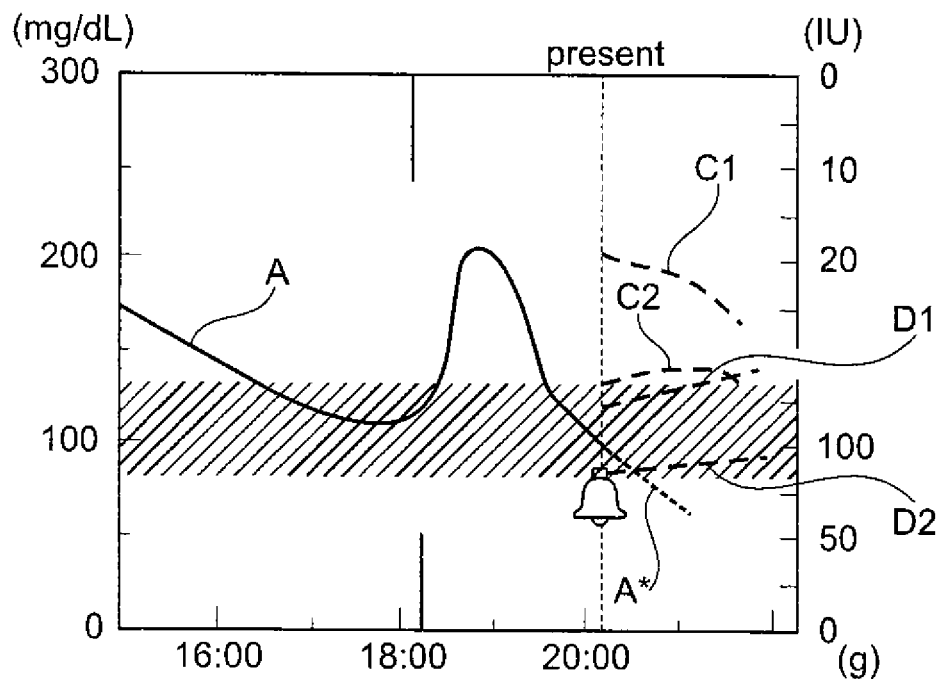

FIG. 4 shows a present situation as follows: last insulin medication (IU; Δ min): 12; −120; and last carb intake (g; Δ min): 54; −120, current blood glucose level (100 mg/dl), expected blood glucose value change (Δ mg/dl): −40,0; course (Δ min): 60,0; and therefore blood glucose value trend (mg/dl/min): −0,67. Based on such present characteristics curve A* is determined.

There are two event-specific characteristic settings related to an event "exercise" (curves C1, C2) and event "car driving" (curves D1, D2), respectively. In the process of the safety check it will be concluded that in view of the present characteristics including the expected curve progression A* both events are not allowed for the user as the expected curve progression A* leaves borders (limits) indicated by the curves C1, C2 and D1, D2. Therefore, the characteristic monitoring apparatus 1 will output information to the user through the display device 3 which indicates that the user is not allowed to start the events characterized by the setting checked.

Figure 5:
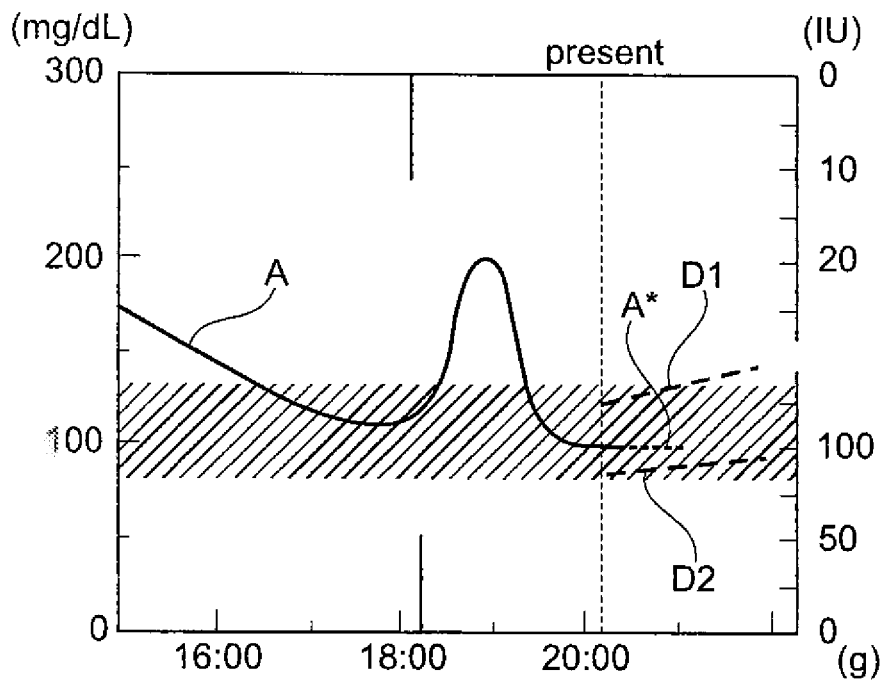
Figure 6:
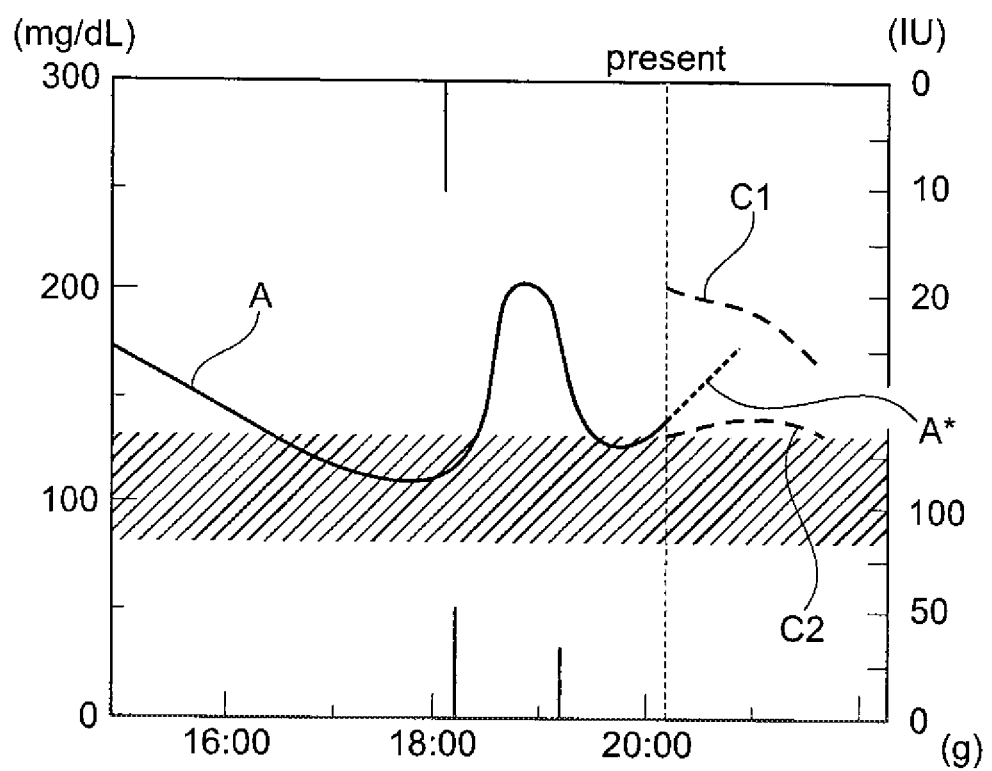

FIGS. 5 and 6 show other present situations as follows. Referring to FIG. 5, the following present characteristics are derived from the curve A of the continuously measured blood glucose values: last insulin medication (IU; Δ min): 12; −120; and last carb intake (g; Δ min): 54; −120, current blood glucose level (100 mg/dl), expected blood glucose value change (Δ mg/dl): 0; course (Δ min): 60,0; and therefore blood glucose value trend (mg/dl/min): 0. Curve A* determined based on such present characteristics is compared to the event-specific characteristics setting for the event "car driving" (curves D1, D2). The characteristic monitoring apparatus 1 will inform the user that event starting is allowed.

Referring to FIG. 6, the following present characteristics are determined from the curve of the continuously measured blood glucose values: last insulin medication (IU; Δ min): 12; −120; and last carb intake (g; Δ min): 36; −60, current blood glucose level (145 mg/dl), expected blood glucose value change (Δ mg/dl): 50,0; course (Δ min): 60,0, and therefore blood glucose value trend (mg/dl/min): 0,83. Curve A* determined based on such present characteristics is compared to the event-specific characteristics setting for the event "car driving" (curves D1, D2). Again, the characteristic monitoring apparatus 1 will inform the user that event starting is allowed.

Figure 7:
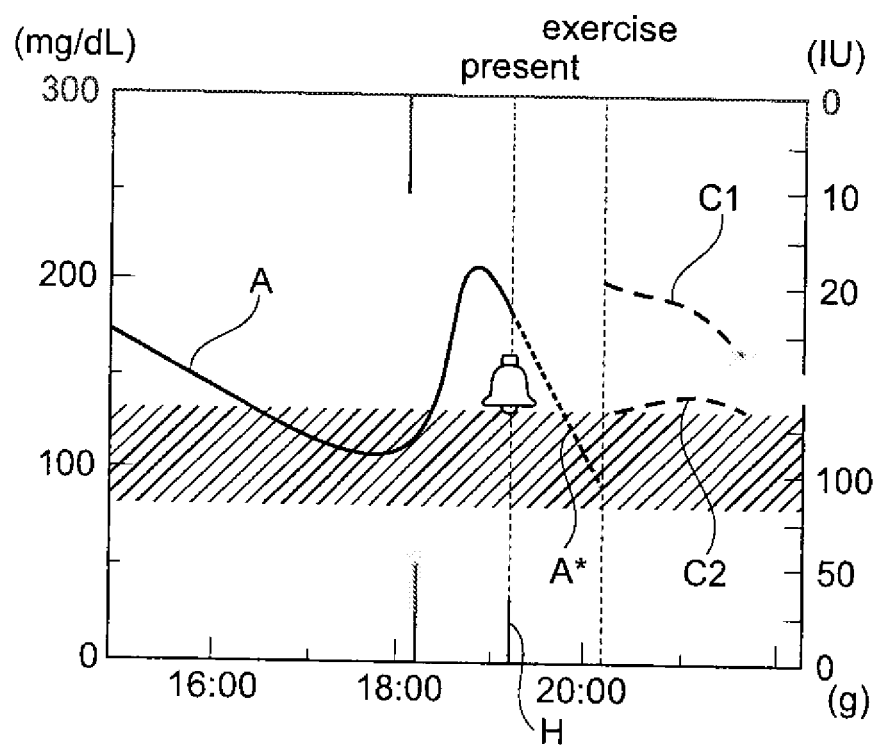
Figure 8:
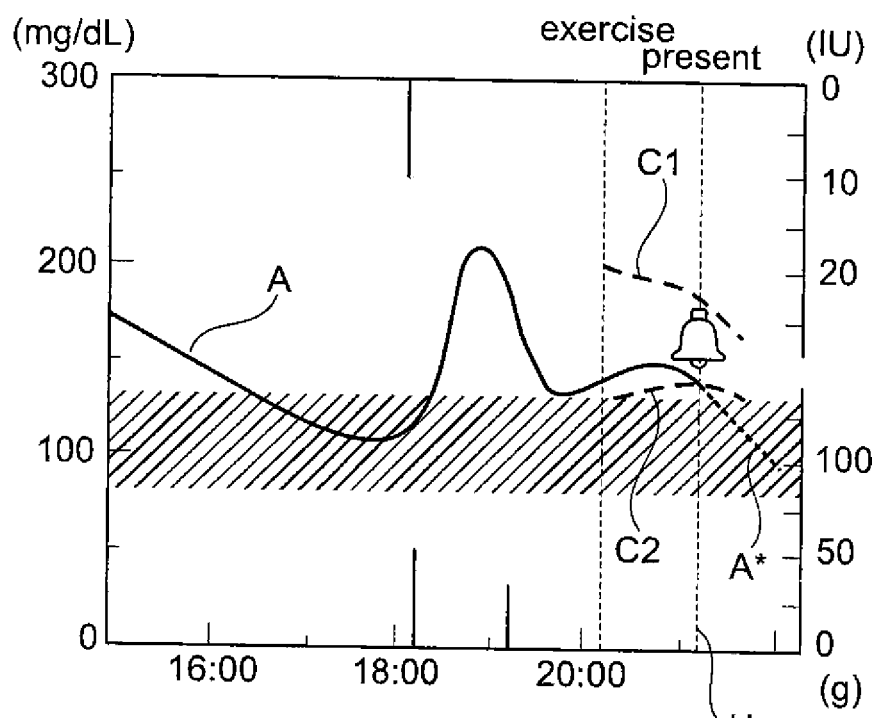

Referring to FIGS. 7 and 8, cases are shown for which present characteristics related to the user will not or do no longer fulfill that event-specific characteristic settings. After processing the information, the characteristic monitoring apparatus 1 will be signalling the user properly by outputting helping resp. warning information.

FIG. 7 refers to the situation that an event "exercise" shall start in 60 minutes (min).

The following present characteristics are provide (curve A): last insulin medication (IU; Δ min): 12; −60; and last carb intake (g; Δ min): 54; −120, current blood glucose level (180 mg/dl), expected blood glucose value change (Δ mg/dl): −100,0; course (Δ min): 60,0; and therefore blood glucose value trend (mg/dl/min): −1,67. This has to be matched to the event-specific characteristic setting (curves C1, C2). In this case the characteristic monitoring apparatus 1 will be signalling the user a helping information by proposing, for example, a carb intake of 36 g. A graphical representation of this is provided by a column H in FIG. 7. The characteristic monitoring apparatus 1 may automatically start another safety check a few minutes before the proposed event starting. Thereby, prior to the proposed event starting, it will be checked whether the proposed carb intake will result in the expected change of the event specific characteristics.

FIG. 8 refers to the situation of having an event "exercise" started 60 min before. The following current characteristics are provided: last insulin medication (IU; Δ min): 12; −180; and last carb intake (g; Δ min): 36; −120, current blood glucose level (140 mg/dl), expected blood glucose value change (mg/dl): −50,0; course (Δ min): 60,0; and therefore blood glucose value trend (mg/dl/min): −0,83. This is matched to the event-specific characteristic settings (curves C1, C2). In this case the characteristic monitoring apparatus 1 will be signalling a warning signal including a helping information by proposing a carb intake of 24 g. A graphical representation of this is provided by a column H in FIG. 8.

While this invention has been described as having an exemplary design, the present invention may be further modified within the spirit and scope of this disclosure. This application is therefore intended to cover any variations, uses, or adaptations of the invention using its general principles.

What is claimed is:

1. A method for characteristic monitoring in conjunction with a mode of continuously measured blood glucose values in a user, in a monitor apparatus provided with a processor, a memory, a data interface, an input device, and a signaling device, the method comprising:

providing a first set of event specific characteristics of a continuous blood glucose monitoring assigned to a first event in the processor, the first set of event specific characteristics being different from a second set of event specific characteristics of the continuous blood glucose monitoring assigned to a second event which is different from the first event;

using a glucose sensor device to continuously measure a glucose level of a user and produce a signal comprising blood glucose value data corresponding to the continuously measured glucose level;

communicating the blood glucose value data to the monitor apparatus;

providing the blood glucose value data and/or characteristic values derived from the blood glucose value data to the processor;

performing a safety check by comparing the set of event specific characteristics of a selected event of the first and second events to present characteristics of the continuous blood glucose monitoring derived from the blood glucose value data and/or the characteristic values by the processor;

generating by the processor a warning signal indicating an event activity related to the selected event shall not be started, if one or more of the present characteristics do not match the assigned characteristic from the set of event specific characteristics of the selected event, otherwise generating a safety signal indicating that it is safe to start the event activity related to the selected event;

outputting an output signal according to the warning signal or the safety signal by the signaling device, the output signal comprising at least one of a visual signal and an acoustic signal;

wherein one of the first and second sets of event specific characteristics is provided by the processor in response to receiving user input data via the input device;

wherein the user input data comprises event selection data selecting one of a first event and a second event and a proposed time at which the selected event is to begin, and wherein the processor provides the first set of event specific characteristics upon selection of the first event and provides the second set of event specific characteristics upon selection of the second event;

wherein, in case of generating the warning signal, a help signal is generated by the processor and outputted by the signaling device, the help signal providing information about proposed user action aiming at matching of the present characteristics with the assigned characteristic from the selected set of event specific characteristics, wherein, after the help signal is outputted, a follow-up safety check is performed before event activity related to the selected event is started and application of the selected set of event specific characteristics is begun and wherein the follow-up safety check is performed at a time which precedes the proposed time by a predetermined time period or is performed after a predefined time period following the warning signal wherein each event has a specific predefined time period;

wherein the help signal includes a recommendation regarding carbohydrate intake or changing the frequency or quantity of administered insulin; and administering carbohydrates or insulin to the user in accordance with the recommendation.

2. The method according to claim 1, wherein a starting first set of event specific characteristics is provided in the memory.

3. The method according to claim 1, wherein for at least one of the first set of event specific characteristics and the second set of event specific characteristics the user input data comprises event definition data defining or redefining one or more characteristics from the first set of event specific characteristics.

4. The method according to claim 1, wherein, at least with respect to the first set of event specific characteristics, the processor is implementing a self-learning procedure by analyzing former events and/or current events and adjusting one or more characteristics from the first set of event specific characteristics.

5. The method according to claim 1, wherein at least one of first set of event specific characteristics and the second set of event specific characteristics is provided with a set of weighted event specific characteristics.

6. The method of claim 5 wherein the step of performing the safety check involves identifying a subset of event specific characteristics and requiring satisfaction of the subset of event specific characteristics to generate a safety signal and wherein the remaining event specific characteristics do not require satisfaction to generate a safety signal.

7. The method according to claim 1, wherein the steps of performing the safety check, generating the warning/safety signal and providing the output signal are repeated by the processor after receiving a user input indicating that the event activity related to the first event was started.

8. The method according to claim 1, wherein the follow-up safety check is performed after a predefined time period wherein each event has a specific predefined time period.

9. The method according to claim 8, wherein the predefined time period of each event is set by the user.

10. The method according to claim 8 wherein the safety check is repeatedly performed at an interval defined by the predefined time period and wherein a starting signal is generated when the present characteristics satisfy the selected set of event specific characteristics for the selected event.

11. The method according to claim 1, wherein at least one of first set of event specific characteristics and the second set of event specific characteristics comprises one or more characteristics selected from the following group: blood glucose value from a continuous measurement, trend or slope of a continuous blood glucose monitoring curve, time to event, time of insulin medication, insulin medication information, food intake time, and food intake information.

12. The method of claim 1 further comprising the step of optimizing the performance of the monitor apparatus by changing the event specific characteristics of an event or suggesting to the user to change the event specific characteristics of an event when the safety check for that event determined it was safe to start or continue the event activity related to the event and the blood glucose value data generated during the event represents an undesirable condition for the user and wherein the suggested changes are based upon a statistical evaluation of data corresponding to a plurality of past selections of the event.

13. The method of claim 12 wherein the determination of whether the blood glucose value data generated during the event represents an undesirable condition for the user includes comparing the slope and value of the blood glucose value data with predefined limits, the predefined limits defining an upper bound and a lower bound for the value of the blood glucose value data for each of the first and second sets of event specific characteristics and wherein the upper and lower bounds for the first and second sets of event specific characteristics vary as a function of time.

14. The method of claim 13 wherein the event specific characteristics define a set of entry criterion which define if it is safe to begin or continue an event and wherein the suggested changes to the event specific characteristics change the entry criterion for the event; and wherein the upper bound and lower bound for the value of the blood glucose value data for each of the first and second sets of event specific characteristics define adherence criterion and the method further includes monitoring whether the blood glucose values remain between the upper bound and lower bound for the duration of the event.

15. The method of claim 12 wherein the step of optimizing the performance of the monitor apparatus comprises making a change to the event specific characteristics of an event only after suggesting the change to the user.

16. The method of claim 1 wherein the step of performing a safety check includes warning the user of previous selections of the event that resulted in an undesirable condition for the user.

17. The method of claim 16 wherein the step of warning the user of previous selections of the event that resulted in an undesirable condition for the user includes communicating the percentage of successfully completed occurrences of the event to the user.

18. The method of claim 1 wherein the selected event is selected at least one or more hours in advance of the beginning of the event and further including the step of adjusting the limit values in a pre-event time period immediately preceding the beginning of the event wherein the limit values are adjusted to the optimum conditions for entering the selected event.

19. The method of claim 1 wherein the signaling device provides a menu to a user of the monitor apparatus, wherein the menu includes a first menu item corresponding to the first event and a second menu item corresponding to the second event and wherein the event selection data comprises selection of one of the first and second menu items wherein the processor provides the first set of event specific characteristics upon selection of the first menu item and the processor provides the second set of event specific characteristics upon selection of the second menu item.

20. The method of claim 19 wherein the first and second sets of event specific characteristics comprise entry criterion which must be satisfied to generate a safety signal and wherein if, after performing a safety check, the entry criterion are not satisfied, one or more options other than entering the event are presented to the user.

21. The method of claim 1 wherein the step of administering the carbohydrates or insulin in accordance with the recommendation is performed during the pre-event time period before conducting the follow-up safety check.

22. The method according to claim 21 wherein the follow-up safety check is performed at a time which precedes the proposed time by a predetermined time period.

23. A method of managing blood glucose levels in a user, the method comprising:

providing a monitor apparatus for safety characteristic monitoring in conjunction with a mode of continuously measured blood glucose values, the apparatus comprising:

a processor, a memory, a data interface, an input device, and a signaling device, the input device being adapted to receive manual input from the user to select a set of event specific characteristics, the monitor apparatus being adapted to receive a signal from a glucose sensor device that continuously measures a glucose level of a user and produces a signal comprising blood glucose value data corresponding to the continuously measured glucose level and wherein the monitor apparatus provides the blood glucose value data to the processor;

and wherein the processor is configured to perform the following steps:

providing a first set of event specific characteristics of a continuous blood glucose monitoring assigned to a first event, the first set of event specific characteristics being different from a second set of event specific characteristics of the continuous blood glucose monitoring assigned to a second event which is different from the first event;

receiving the blood glucose value data comprising continuously measured glucose values;

receiving the blood glucose value data and/or characteristic values derived from the blood glucose value data;

performing a safety check by comparing the set of event specific characteristics of a selected event of the first and second events to present characteristics of the continuous blood glucose monitoring derived from the blood glucose value data and/or the characteristic values;

generating a warning signal indicating one of an event activity related to the selected event shall not be started and an event activity related to the selected event and started before shall not be continued, if one or more of the present characteristics do not match the assigned characteristic from the set of event specific characteristics of the selected event, otherwise generating a safety signal indicating that it is safe to start the event activity related to the selected activity or, if the selected activity has already started, that it is safe to continue the event activity related to the selected activity;

providing the warning signal or the safety signal to the signaling device for outputting an output signal according to the warning signal or the safety signal by the signaling device, the output signal comprising at least one of a visual signal and an acoustic signal wherein the output signal communicates to the user that the event activity related to the selected activity shall not be started, that the event activity related to the selected activity shall not be continued, that it is safe to start the event activity related to the selected activity or that it is safe to continue the event activity related to the selected activity;

wherein one of the first and second sets of event specific characteristics is provided by the processor in response to receiving user input data via the input device;

wherein the user input data comprises event selection data selecting one of a first event and a second event wherein the processor provides the first set of event specific characteristics upon selection of the first event and provides the second set of event specific characteristics upon selection of the second event;

wherein when the selected event is selected at least one or more hours in advance of the beginning of the event, the method further includes the step of adjusting the limit values in a pre-event time period immediately preceding the beginning of the event wherein the limit values are adjusted to the optimum conditions for entering the selected event and, when the selected event is not selected in advance, the set of event specific characteristics of the selected event are applied without adjusting the limit values in a pre-event time period; and wherein, in case of generating the warning signal, a help signal is generated by the processor and outputted by the signaling device wherein the help signal includes a recommendation regarding carbohydrate intake or changing the frequency or quantity of administered insulin; and administering carbohydrates or insulin to the user in accordance with the recommendation.

24. The method of claim 23 wherein the processor is configured to optimize the performance of the monitor apparatus by changing the event specific characteristics of an event or suggesting to the user to change the event specific characteristics of an event when the safety check for that event determined it was safe to start or continue the event activity related to the event and the blood glucose value data generated during the event represents an undesirable condition for the user.

25. The method of claim 24 wherein the determination of whether the blood glucose value data generated during the event represents an undesirable condition for the user includes comparing the slope and/or value of the blood glucose value data with predefined limits.

26. The method of claim 23 wherein the limit values adjusted in the pre-event time period include the slope and value of a curve representing the continuously measured glucose values.

27. The method of claim 23 wherein the processor is further configured to perform the step of recommending carbohydrate intake or changing the frequency or quantity of administered insulin during the pre-event time period to thereby facilitate the satisfaction of the limit values.

* * * * *